(12) United States Patent
Mata et al.

(10) Patent No.: US 10,314,354 B2
(45) Date of Patent: Jun. 11, 2019

(54) APPARATUS AND METHOD FOR PERSPIRATION MANAGEMENT ON THE HUMAN BODY

(71) Applicants: Pedro P. Mata, Fairfield, CT (US); Daniel Blank, Fairfield, CT (US)

(72) Inventors: Pedro P. Mata, Fairfield, CT (US); Daniel Blank, Fairfield, CT (US)

(*) Notice: Subject to any disclaimer, the term of this patent is extended or adjusted under 35 U.S.C. 154(b) by 401 days.

(21) Appl. No.: 14/986,693

(22) Filed: Jan. 3, 2016

(65) Prior Publication Data
US 2016/0242480 A1   Aug. 25, 2016

Related U.S. Application Data

(60) Provisional application No. 62/100,187, filed on Jan. 6, 2015.

(51) Int. Cl.
| | | |
|---|---|---|
| *A41D 20/00* | (2006.01) | |
| *A41D 31/02* | (2019.01) | |
| *B32B 5/06* | (2006.01) | |
| *B32B 5/08* | (2006.01) | |
| *B32B 27/12* | (2006.01) | |
| *A61B 1/00* | (2006.01) | |
| *B32B 5/02* | (2006.01) | |

(52) U.S. Cl.
CPC .............. *A41D 31/02* (2013.01); *A41D 20/00* (2013.01); *A61B 1/00* (2013.01); *B32B 5/024* (2013.01); *B32B 5/06* (2013.01); *B32B 5/08* (2013.01); *B32B 27/12* (2013.01); *A41D 2400/62* (2013.01); *B32B 2262/0261* (2013.01); *B32B 2262/0276* (2013.01); *B32B 2262/062* (2013.01); *B32B 2262/065* (2013.01); *B32B 2262/14* (2013.01); *B32B 2307/546* (2013.01); *B32B 2307/726* (2013.01); *B32B 2307/7265* (2013.01); *B32B 2535/00* (2013.01); *B32B 2571/00* (2013.01)

(58) Field of Classification Search
CPC .... A41D 20/00; A41D 31/02; A41D 2400/62; B32B 5/024; B32B 5/06; B32B 5/08; B32B 27/12
USPC .............................................. 2/69
See application file for complete search history.

(56) References Cited

U.S. PATENT DOCUMENTS

| | | | | |
|---|---|---|---|---|
| 1,139,942 A | * | 5/1915 | Wightman et al. | B43M 11/04 118/201 |
| 1,633,586 A | * | 6/1927 | Hunter | A61F 13/122 128/DIG. 23 |
| 2,783,474 A | * | 3/1957 | Campagna | A41D 20/00 2/171 |

(Continued)

FOREIGN PATENT DOCUMENTS

| | | |
|---|---|---|
| CN | 103120383 A | 5/2013 |
| WO | WO 1986000197 A1 | 1/1986 |

*Primary Examiner* — Joshua E Rodden
(74) *Attorney, Agent, or Firm* — McCarter & English, LLP; David J. Silvia

(57) ABSTRACT

The invention is an apparatus and method used to ergonomically remove and manage perspiration on the human body during exercise, manual labor, or any activity that requires the removal of perspiration. The apparatus is constructed from moisture absorbing, wicking and elastic materials fashioned as a sleeve or wrap and positioned on the body at locations that the wearer would remove sweat through natural body movement.

13 Claims, 2 Drawing Sheets

(56) References Cited

U.S. PATENT DOCUMENTS

| | | | |
|---|---|---|---|
| 4,244,057 A * | 1/1981 | Burnham | A41D 19/0024 2/160 |
| 4,603,440 A | 8/1986 | Hale | |
| 4,742,581 A * | 5/1988 | Rosenthal | A41D 20/005 2/170 |
| 4,843,653 A * | 7/1989 | Coble | A41D 20/00 2/170 |
| 5,014,360 A * | 5/1991 | Smith | A41D 13/0015 2/115 |
| 5,090,060 A * | 2/1992 | Gates | A41D 13/0015 2/115 |
| 5,305,470 A * | 4/1994 | McKay | A41D 20/005 2/170 |
| 5,555,564 A * | 9/1996 | Welch | A41B 11/00 2/22 |
| 5,706,521 A * | 1/1998 | Haney | A41D 19/0024 2/160 |
| 5,826,277 A * | 10/1998 | McConville | A41D 20/00 2/171 |
| 5,915,532 A * | 6/1999 | Williams | A41D 20/00 2/171 |
| 6,971,122 B2 * | 12/2005 | Sanchez | A41D 20/00 2/174 |
| 7,383,588 B2 * | 6/2008 | Victor | A41D 20/00 2/16 |
| 7,752,681 B2 | 7/2010 | Michel | |
| 7,766,014 B2 * | 8/2010 | Piret | A61F 13/12 128/200.24 |
| 8,209,776 B1 * | 7/2012 | Aragon | A41D 20/00 2/16 |
| 8,898,812 B2 | 12/2014 | Thompson et al. | |
| 8,910,312 B1 * | 12/2014 | Apisa | A41D 27/12 2/170 |
| 2002/0073475 A1 * | 6/2002 | Bloom | A41D 3/02 2/69 |
| 2004/0031120 A1 * | 2/2004 | Cherian | A41D 19/0024 15/227 |
| 2007/0118943 A1 * | 5/2007 | Stockhamer | A41D 1/04 2/1 |
| 2007/0234466 A1 * | 10/2007 | Stengel | A41D 19/0024 2/160 |
| 2009/0112143 A1 * | 4/2009 | Fournet, II | A61F 13/10 602/57 |
| 2010/0031411 A1 * | 2/2010 | Andrews | A41D 19/0017 2/20 |
| 2011/0016610 A1 * | 1/2011 | Wieder | A41D 20/00 2/170 |
| 2011/0247125 A1 * | 10/2011 | Fournier | A41D 20/00 2/170 |
| 2014/0173806 A1 * | 6/2014 | Fournier | A41D 20/00 |
| 2016/0262470 A1 * | 9/2016 | Blythe | A41D 20/00 |
| 2016/0361015 A1 * | 12/2016 | Wang | A61B 5/6832 |

* cited by examiner

APPARATUS AND METHOD FOR PERSPIRATION MANAGEMENT ON THE HUMAN BODY

CROSS-REFERENCE TO RELATED APPLICATIONS

The present applications claims priority to the earlier filed provisional application having U.S. APPLICATION No. 62/100,187, with a FILING DATE of Jan. 6, 2015, and NAME OF APPLICANT(s) being Pedro P. Mata and Daniel Blank, and TITLE OF INVENTION of "Apparatus for Perspiration Wicking and Moisture Management on the Body" and hereby incorporates subject matter of the provisional application in its entirety.

PATENT CITATIONS

| Cited Patent | Filing Date | Publication Date | Applicant | Title |
| --- | --- | --- | --- | --- |
| U.S. Pat. No. 8,898,812 | Oct. 26, 2011 | Dec. 12, 2014 | William Thompson | Garment Having Integrated Perspiration Barriers |
| U.S. Pat. No. 4,603,440 | Sep. 19, 1984 | Aug. 5, 1986 | James M. Hale | Sport Jersey |
| U.S. Pat. No. 7752681 B2 | May 27, 2003 | Jul. 13, 2010 | Joyce Michel | Article Of Clothing With Wicking Portion |
| WO 1986000197 | Jun. 18, 1985 | Jan. 16, 1986 | Joel Michael Haire | Absorbent Headband or Sweatband |
| CN 103120383 A | Nov. 19, 2011 | May 29, 2013 | 张英 | Antimicrobial and sweat absorbing T-shirt |

FIELD OF CLASSIFICATION SEARCH

CPC: A41D 20/00, A41D 27/13, A42C 5/02, A41D 2400/60, A41D 2600/20

STATEMENT REGARDING FEDERALLY SPONSORED RESEARCH OR DEVELOPMENT

N/A

REFERENCE TO A SEQUENCE LISTING, A TABLE, OR A COMPUTER PROGRAM, LISTING COMPACT DISC APPENDIX

N/A

BACKGROUND OF THE INVENTION

1. Technical Field of Invention

The present invention relates to a garment for the removal and management of perspiration from the wearer during any act of physical exertion including exercise, work, and play. The present invention is unique in its use of materials, design, shape, construction, and the placement by the wearer on their body.

2. Description of the Related Art

It is human nature to naturally gravitate and seek specific regions of the body to eliminate or remove perspiration that is collected and produced in other regions of the body. Active people will often try to remove perspiration from their forehead with their own hand and then wipe it off on their apparel or try to wipe it off directly with a sleeve or other area of their shirt or a towel. These methods are not effective for removing or managing perspiration and merely transfer the moisture from one body part to another or result in saturating a material not designed to absorb large amounts of moisture.

Other current art, such as sweat bands, head bands, and towels, are typically constructed of Terrycloth cotton and form a single material on all internal and external surfaces. As such, they are poor at removing perspiration once they have reached their saturation point. Additionally, limitations of the absorption capabilities of Terrycloth prevent the transport of perspiration away from the sweat band. The use of a towel is inconvenient during the course of regular physical activity as it is not persistently available to the user and requires the user to utilize a free hand to manipulate the towel. Finally, current art has not been designed to be placed on other areas of the body which are natural removal points of perspiration such as the forearm, upper arm, torso, thighs, calves, buttocks, and back of the hand.

For example, intense fitness activities such as cross training, spinning, group fitness and hot yoga cause participants to produce excessive perspiration. Current art does not utilize advanced absorptive materials now available to effectively remove and manage the excessive perspiration of today's athletes, nor do they offer the flexibility of the user to locate said inventions to desired areas of the body that will not interfere with the performance of the wearer's activity. Typically, these athletic activities require the user to maintain control of their hands and concentration in order to perform the activity which is not adequately serviced by current art, such as towels. In addition to exercise and athletics, perspiration-inducing environments exist for many professionals in occupational fields such as culinary, medical, construction and industrial jobs, which are also not well served by current art.

As will be set forth hereinbelow, the present invention is a novel apparatus and method to intuitively and ergonomically remove and manage perspiration on the human body during exercise, athletics, manual labor or during any activity that requires the removal of perspiration while enhancing comfort and performance for the wearer. The apparatus is composed of unique materials that have not been previously applied for this purpose.

The apparatus is designed to utilize perspiration-absorbing materials with superior absorption rates and greater moisture holding capacity than prior inventions. These highly absorptive materials are used in combination with perspiration wicking materials to transport unwanted perspiration away from the contact point of the apparatus and the wearer. Additionally, the invention incorporates materials with elastic properties to secure the apparatus onto specific regions of the body facilitating the method of use. This method by which the apparatus is employed allows the wearer to naturally remove and manage perspiration without the apparatus interfering with the wearer and their current activity.

BRIEF SUMMARY OF THE INVENTION

This patent covers the method by which humans remove perspiration from their bodies through the utilization of specific perspiration management apparatus that is strategically placed on the body during activities of physical exertion that are likely to produce perspiration.

The apparatus of the present invention is adaptable to be worn on various locations of the wearer's body dependent on the individual and type of activity they are engaged in. The purpose is to make available, easily and naturally to the wearer, an apparatus that is used to remove and collect perspiration from various points of the body. The invention is constructed of absorbent, fast drying and flexible materials used in an optimal configuration of layers to achieve high performance perspiration management that integrates into the active individuals movements. It is produced by combining moisture absorbing materials, moisture wicking materials; and elastic materials to act as a band, wrap, or sleeve. This article is intended for use by individuals during exercise, work, play or any activity that may require enough exertion to cause the individual to perspire. The wrap, as illustrated in FIGS. 1 & 2 below, can be placed on various strategic points on the body that are natural locations for the wearer to utilize the apparatus to remove perspiration and moisture.

Once the invention is in place on the wearer's body and the wearer begins to perspire from exertion, there is no need for instruction on use of the apparatus as the wearer can naturally and intuitively wipe away perspiration in fluid movements that do not interfere with the activity being performed. For example, a runner or cyclist perspiring from their forehead and face would reach up to their head with the absorbent material of the invention covering the back of their hand and wrist to remove the perspiration without distracting from the performance of their activity. Similarly, during the performance of bending or seated Yoga or stretching activities, the participant could remove moisture from their hands by applying the apparatus to their lower leg or calf area, allowing them to conveniently, comfortably and safely continue their activity with dry hands. This alleviates the need for saturating their athletic apparel or using a towel that would be placed on a dirty floor. The apparatus is designed to be washed and reused by the wearer.

BRIEF DESCRIPTION OF THE SEVERAL VIEWS OF THE DRAWING

While the specification concludes with claims particularly pointing out and distinctly claiming the subject matter of the invention, it is believed the invention will be better understood from the following description taken in conjunction with the accompanying drawings, wherein:

DETAILED DESCRIPTION OF THE INVENTION

Figures 1, 2:
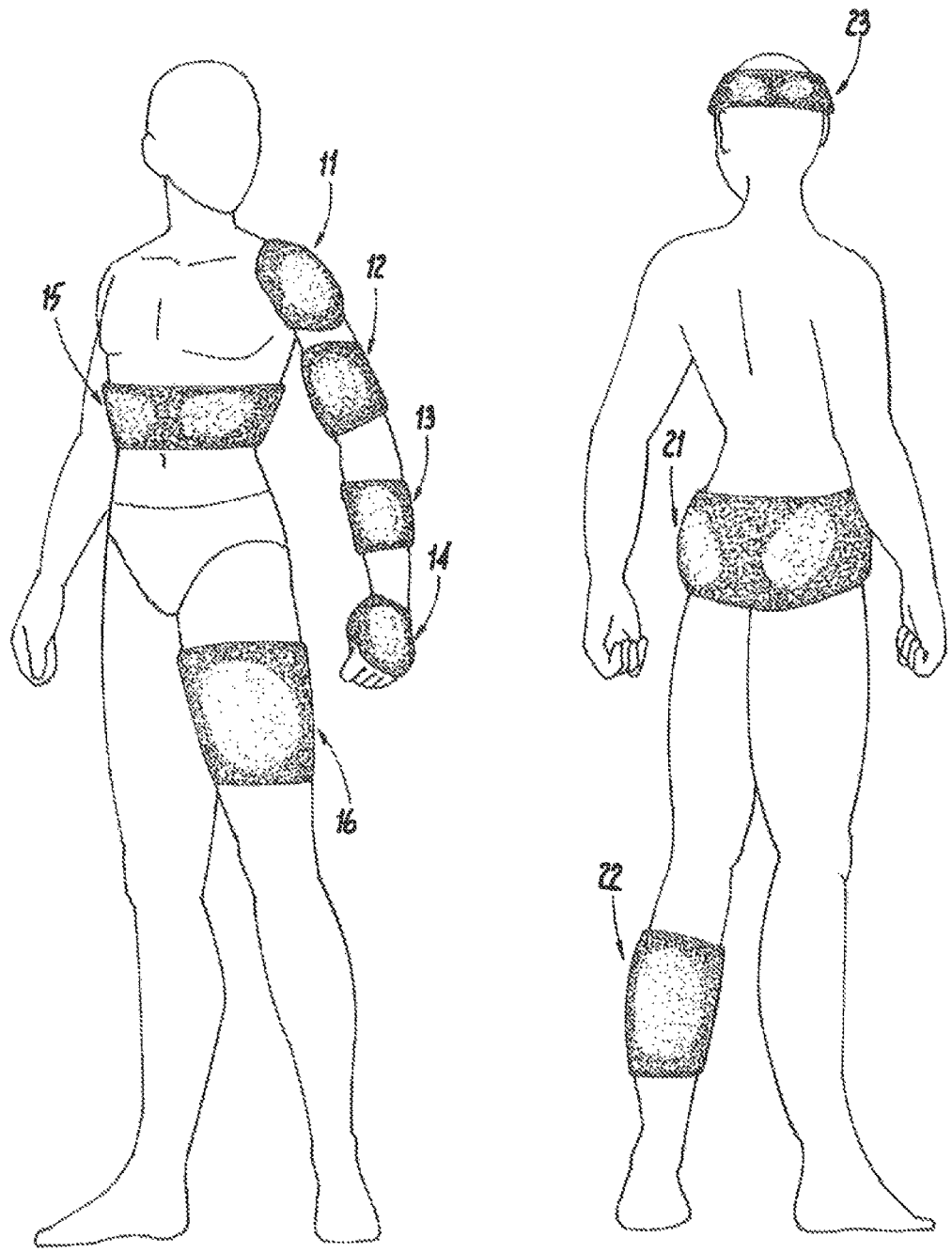
FIG. 1—displays various points on the body that the apparatus can be positioned when viewing the body from the front.
FIG. 2—displays various points on the body that the apparatus can be positioned when viewing the body from the rear.

Referring now more particularly to the accompanying drawings which show several of the preferred embodiments of the invention, FIG. 1 shows the shoulder having a perspiration band 11 positioned specifically with the moisture absorbing material facing forward, upward, and away from the body, specifically positioned to be used to remove moisture from the face, more specifically the cheek. This is accomplished by having the wearer raise the shoulder in a shrugging motion which positions the moisture absorbing material upward and against the side of the face/cheek.

FIG. 1 also shows the bicep/upper arm having a perspiration band 12 positioned specifically with the moisture absorbing materials facing forward and away from the body, specifically positioned to be used to remove moisture from the head, more specifically from the side of the head and ear. This is accomplished by having the wearer wipe the side of the head by raising the arm up and wiping the side of the head utilizing the bicep/upper arm apparatus.

FIG. 1 additionally demonstrates the forearm having a perspiration band 13 positioned specifically with the moisture wicking band positioned upwards and away from the wearer. This position is used to address moisture that gathers on the wearer's forehead and it is intended that the wearer will raise their arm and position the forearm on the forehead and brow of the face to remove moisture.

FIG. 1 further illustrates a perspiration band 14 positioned on the hand in a glove format in which the moisture absorption material is positioned on the top of the hand. This example of the apparatus can be utilized to remove moisture from various positions of the body include, but not limited to, the bottom/palm of the alternate hand, the forehead, the cheek, the side of the neck, and the back of the thigh and calf.

FIG. 1 further demonstrates a perspiration band 15 positioned across the lower torso (or belly) with the moisture absorbing material facing out and away from the body. From this position, the wearer can utilize the band to remove moisture from the various positions of the body including, but not limited to, the palms of the hand, the underside of the forearm, and the fingers.

Lastly, FIG. 1 shows a perspiration band 16 positioned on the thigh of the wearer. The moisture absorbing materials is positioned away from the body. From this point of placement, the wearer can utilize the apparatus to remove perspiration from the hand and forearm.

FIG. 2 shows the perspiration apparatus 21 positioned on the buttock of the wearer on both sides of the body. The moisture absorbing material is positioned away from the body. It is intended that the wearer will utilize the apparatus 21 to remove moisture from the hands.

FIG. 2 further demonstrates a perspiration device 22 being positioned on the calf of the wearer. The moisture absorbent material is positioned away from the body and facing rearward. The device 22 is intended to support the wearer in removing moisture from the hands as well as the alternate calf. Lastly, FIG. 2 additionally illustrates a perspiration device 23 being positioned on the head of the wearer.

Figure 3:
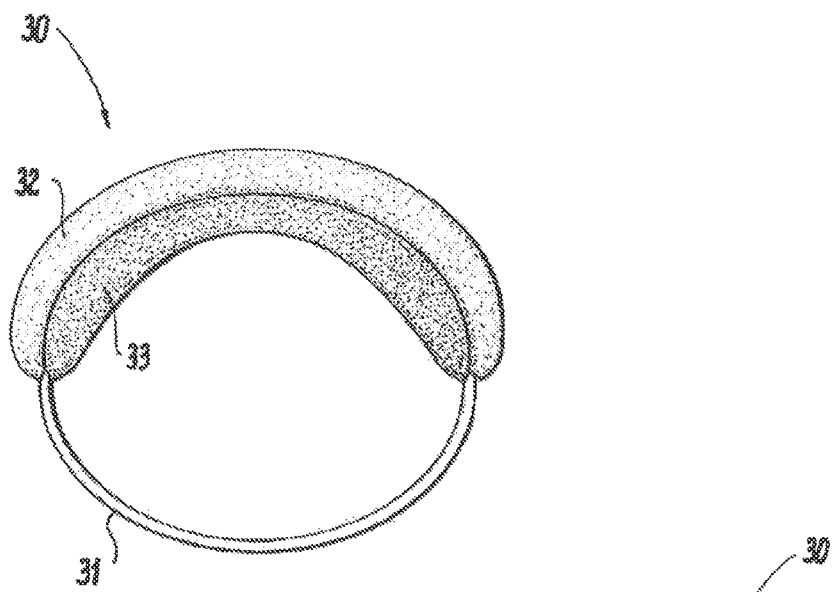
FIG. 3—cross section of the apparatus wrapped around a simulated section of the human body (e.g. forearm, thigh, calf.
Figure 4:
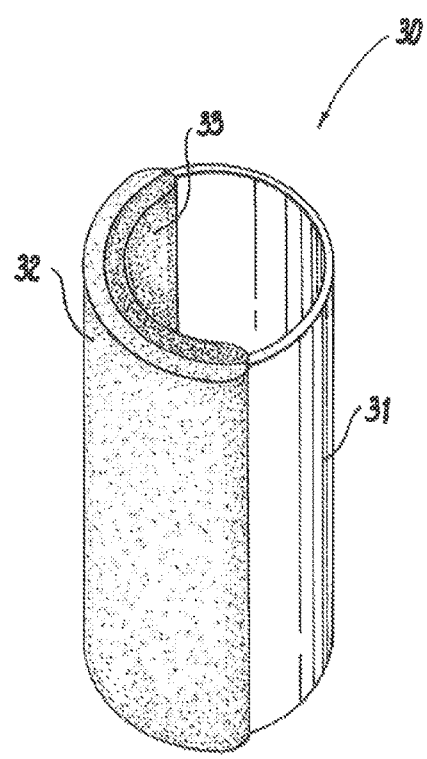
FIG. 4—perspective view of the apparatus wrapped around a simulated section of the human body (e.g. forearm, thigh, calf).

FIG. 3 shows a cross section of a perspiration device 30 as it may appear on various parts of the body including the forearm, bicep, and thigh. It is intended to demonstrate the design of the apparatus as it is intended to use on any part of the body.

Item 31 represents the elastic layer which is comprised of a 4-way stretch material such as Lycra, Spandex, Luan, or similar. This material allows the apparatus to adjust to fit multiple parts of the body and various sized users and conform the apparatus to the shape of the wearer. This elastic property will be the primary mechanism that allows the device to remain positioned on the body of the wearer by means of the compressive properties of the elastic.

Item 32 represents the moisture absorbency layer of the apparatus that is utilized as the mechanism to manage perspiration. This layer contains multiple materials that are woven together as a single element comprised of Cotton, Bamboo, Polyester and other fibrous materials designed to absorb and transfer perspiration away from the surface. The surface being defined as the area that is in direct contact with the air and the point of contact with which the wearer would use the apparatus to remove sweat from other parts of the body (e.g. the forehead). This layer is also designed to distribute perspiration from the surface down the layer in order to maximize absorbency while allowing the surface to absorb more perspiration.

Item 33 serves as an additional wicking layer that transports the perspiration captured in layer 32 and distributes it laterally to increase absorption capacity. This layer additionally provides a barrier between captured perspiration and the wearer's skin inside the apparatus.

The information provided and invention as presented have been described to the inventor's preferred incarnations, it will be understood by those skilled in the art that various changes may be made and elements or materials substituted or modified without departing from the true intent and scope of the invention.

What is claimed is:

1. An apparatus for perspiration management which is adapted to be worn on a wearer's body for removing perspiration and moisture, the apparatus comprising:
   an outer layer made of moisture absorbent material, the outer layer having an upper surface and a lower surface, the upper surface configured to be in direct contact in the air when the apparatus is in use and a point of contact in which a wearer would use the apparatus to remove sweat from other parts of the wearer's body;
   an interior layer made of moisture wicking material in contact with the lower surface of the outer layer of moisture absorbent material; and
   an inner layer of elastic material in contact with the moisture wicking material; and
   wherein the inner layer of elastic material is positioned in contact with the wearer's body and is attached at a first end to a first side of the interior layer and at a second end to a second side of the interior layer, such that the interior layer is in direct contact with the wearer's body when the apparatus is in use such that the interior layer provides a moisture barrier which is adapted for preventing captured moisture from contacting the wearer's body.

2. The apparatus as recited in claim 1, wherein the outer layer of moisture absorbent material is comprised of three layers, a first layer being made of moisture absorbing material containing approximately 70% bamboo and about 30% organic cotton, and a second layer of a different moisture absorbent material and a backing layer of wicking polyester which is arranged adjacent to the interior layer of moisture wicking material.

3. The apparatus as recited in claim 1, wherein an additional inner layer made of a moisture wicking material such as nylon, polyester or a cotton blend is applied as an additional layer of moisture transport and as a protective barrier for the comfort of the wearer.

4. The apparatus as recited in claim 1, wherein the apparatus is adapted to be worn over a lower part of a wearer's hand and covering the wrist and lower forearm.

5. The apparatus as recited in claim 4, further including a thumbhole to provide additional coverage area and greater stability of keeping the apparatus in a desired location.

6. The apparatus as recited in claim 1, wherein the apparatus is adapted to be worn over a wearer's wrist and lower forearm.

7. The apparatus as recited in claim 1, wherein the apparatus is adapted to be worn on a wearer's shoulder.

8. The apparatus as recited in claim 1, wherein the apparatus is adapted to be worn on a wearer's bicep/upper arm.

9. The apparatus as recited in claim 1, wherein the apparatus is adapted to be worn on a wearer's lower torso.

10. The apparatus as recited in claim 1, wherein the apparatus is adapted to be worn on a wearer's thigh/upper leg.

11. The apparatus as recited in claim 1, wherein the apparatus is adapted to be worn on a wearer's calf.

12. The apparatus as recited in claim 1, wherein the apparatus is adapted to be worn on a wearer's buttocks.

13. The apparatus as recited in claim 1, wherein the apparatus is adapted to be worn on a wearer's head.

* * * * *